(12) United States Patent
Vignoud et al.

(10) Patent No.: US 9,228,955 B2
(45) Date of Patent: Jan. 5, 2016

(54) SYSTEM AND METHOD FOR DETECTING ANALYTES PRESENT IN A GAS SAMPLE

(75) Inventors: Severine Vignoud, Bernin (FR); Michael Descamps, Montreuil (FR); Francois Perraut, Saint Joseph de Riviere (FR); Anne Planat-Chretien, Saint-Egreve (FR); Emmanuelle Schultz, Saint-Egreve (FR)

(73) Assignee: Commissariat a l' energie atomique et aux energies alternatives, Paris (FR)

( * ) Notice: Subject to any disclaimer, the term of this patent is extended or adjusted under 35 U.S.C. 154(b) by 511 days.

(21) Appl. No.: 13/218,750

(22) Filed: Aug. 26, 2011

(65) Prior Publication Data

US 2012/0113421 A1    May 10, 2012

(30) Foreign Application Priority Data

Aug. 31, 2010    (FR) ...................................... 10 56909

(51) Int. Cl.
| | | |
|---|---|---|
| *G01N 21/00* | (2006.01) | |
| *G01N 21/55* | (2014.01) | |
| *G01J 3/30* | (2006.01) | |
| *G01N 21/78* | (2006.01) | |
| *G01N 21/05* | (2006.01) | |
| *G01N 21/77* | (2006.01) | |
| *G01N 21/03* | (2006.01) | |

(52) U.S. Cl.
CPC .............. *G01N 21/783* (2013.01); *G01N 21/05* (2013.01); *G01N 2021/0346* (2013.01); *G01N 2021/7783* (2013.01); *G01N 2021/7786* (2013.01)

(58) Field of Classification Search
CPC ... G01N 21/274; G01N 21/55; G01N 21/783; G01N 2021/3155
USPC .......................................... 356/311, 432–445
See application file for complete search history.

(56) References Cited

U.S. PATENT DOCUMENTS

| | | | | |
|---|---|---|---|---|
| 2004/0126279 | A1* | 7/2004 | Renzi et al. .................... | 422/100 |
| 2005/0062972 | A1* | 3/2005 | Krusen .......................... | 356/437 |

(Continued)

FOREIGN PATENT DOCUMENTS

| | | |
|---|---|---|
| FR | 2 890 745 A1 | 3/2007 |
| WO | WO 2007/031657 A2 | 3/2007 |

OTHER PUBLICATIONS

European Search Report issued Sep. 7, 2011, in European Patent Application No. 11 17 8862 with English Translation of Category of Cited Documents.

(Continued)

*Primary Examiner* — Tarifur Chowdhury
*Assistant Examiner* — Sunghee Y Gray
(74) *Attorney, Agent, or Firm* — Oblon, McClelland, Maier & Neustadt, L.L.P.

(57) ABSTRACT

Provided is a system for detecting analytes of interest present in a gas sample, including a layer of porous material, positioned at the surface of a substrate so as to extend longitudinally along a fluidic flow path of the gas sample, said porous material containing a plurality of probe molecules, each probe molecule being able to react with the analyte of interest by causing a change in the spectral properties of said probe molecule. Also included is a a pump for generating a flow of the gas sample along the fluidic path so that the gas sample comes into contact with said layer of porous material. The system also includes at least one optical detection device capable of successively detecting, at distinct detection areas of said porous material layer distributed along said fluidic path, a change in the spectral properties of at least one of said probe molecules.

16 Claims, 4 Drawing Sheets

(56) References Cited

U.S. PATENT DOCUMENTS

| 2008/0245971 | A1 |   | 10/2008 | Wimberger-Friedl et al. |       |
|--------------|----|---|---------|-------------------------|-------|
| 2009/0068668 | A1 | * | 3/2009  | Duer                    | 435/6 |
| 2009/0216097 | A1 | * | 8/2009  | Wilson et al.           | 600/327 |
| 2009/0279093 | A1 | * | 11/2009 | Van Herpen et al.       | 356/417 |
| 2011/0059538 | A1 | * | 3/2011  | Weiss et al.            | 436/86 |

OTHER PUBLICATIONS

E. Schultz, et al., "A novel fluorescence-based array biosensor: Principle and application to DNA hybridization assays", Biosensors and Bioelectronics, vol. 23, No. 7, XP022440001, Oct. 22, 2007, pp. 987-994.

L. Tao, et al., "Surface energy induced patterning of organic and inorganic materials on heterogeneous Si surfaces", Journal of Vacuum Science and Technology: Part B, vol. 25, No. 6, XP012105405, Dec. 6, 2007, pp. 1993-1997.

Wenchuang Hu, et al, "Surface Energy Induced Patterning of Polymer Nanostructures for Cancer Diagnosis and Therapy", Proceedings of the 7th IEEE International Conference on Nanotechnology, XP 031307777, Aug. 2-5, 2007, pp. 295-300.

* cited by examiner

SYSTEM AND METHOD FOR DETECTING ANALYTES PRESENT IN A GAS SAMPLE

TECHNICAL FIELD

The present invention relates to the general field of detection of analytes of interest present in a gas sample. These analytes may be chemical, biological or biochemical compounds present in a gas environment.

STATE OF THE PRIOR ART

In many fields, it is sought to produce, analyze a gas environment or a gas sample with the purpose of for example detecting chemical, biological or biochemical compounds present.

This is notably the case of the field of clinical diagnosis, where it may be sought to detect bio-markers of diseases in breath samples of persons, of monitoring of the environment, in particular of the quality of air, or of the field for monitoring industrial activities, for example for analyzing industrial effluents, or monitoring of personnel exposed to volatile organic compounds.

Patent application WO 2007/031657, notably filed in the name of the applicant, describes a system for detecting analytes of interest present in a gas sample. This detector allows detection of formaldehyde, a compound classified as carcinogenic and particularly present in certain building products used in the building industry.

The detection system comprises a fluidic chamber including a gas inlet orifice and a gas outlet orifice. The gas sample is intended to flow from the inlet orifice to as far as the outlet orifice, following a preferential fluidic flow path.

Inside the fluidic chamber is deposited a thin layer of a nanoporous sol-gel material. The nanoporous sol-gel material contains probe molecules capable of reacting with formaldehyde, for example Fluoral-P, which causes a variation of its spectral properties.

Thus, when the gas sample flows into the fluidic chamber, it naturally comes into contact with the thin layer of nanoporous sol-gel material and is introduced into the latter, because of the porosity of the material. The probe molecules then react with the formaldehydes, which is expressed by a change in the spectral properties of these probe molecules.

With an optical detection device it is possible to detect said change in the spectral properties of the probe molecules before and after reaction with formaldehyde, notably a variation of the absorbance or fluorescence spectra thereby allowing the system to detect the presence of analytes of interest in the gas sample.

For this it comprises an excitation light source and an optical collector. The excitation light source illuminates the whole of the nanoporous sol-gel material layer according to a determined wavelength or over a given spectrum of wavelengths, and the collector receives the transmitted or reflected light or the light emitted by fluorescence.

The nanoporous sol-gel material thin layer thus forms a three-dimensional detection area, the surface area of which for adsorbing and/or binding analytes, because of its three-dimensional structure and of the size of the pores, is very large.

Further, this material is particularly suitable for the analysis of gas samples. Indeed, the hydraulic resistance $R_h$ to the flow of a fluid in a porous material is substantially proportional to $\mu_f/d^4$, wherein $\mu_f$ is the dynamic viscosity of the fluid and d is the average pore size. It is understood that the resistance toward a liquid is at least a thousand times higher than the resistance towards a gas. The hydraulic resistance in the case of a liquid may therefore be very high and thereby prevent the flow of the latter in the material.

Moreover, the low dynamic viscosity of the gas thus allows the use of a material with a very small average pore size, which thus increases the surface area for adsorbing and/or binding analytes.

However, this detection device has a certain number of drawbacks.

Thus, the material used in this example of the prior art is a sol-gel material deposited with the known technique of <<dip-coating>>, which does not allow delimitation of the general shape of the material. The thin layer thus has a general shape which does not necessarily coincide with the fluidic path of the gas sample. Certain areas of the thin layer are therefore not or very little covered by the gas sample.

Moreover, the excitation light source illuminates the whole of the thin layer. It thus illuminates at the same time, spatial areas of the thin layer having significant reaction level and spatial areas with low reaction level. The response signal to the light excitation, received by the optical collector, is therefore spatially heterogeneous, which is detrimental to the resolution of the detector.

Moreover, the excitation light source is capable of illuminating areas of the thin layer which are not directly located in the fluidic path of the gas sample. These areas therefore do not respond or only very little to the light excitation which is sent to them, thereby decreasing the resolution of the detector.

Finally, the detector has a sensitivity which tends to degrade over time. Indeed, the probe molecules which have reacted with an analyte and have responded by absorbance or fluorescence to the light excitation, no longer respond to subsequent light excitations. Also, the amount of probe molecules capable of reacting with the analyte and responding to a light excitation decreases over time, thus decreasing the sensitivity of the detector.

Another example of a system for detecting analytes of interest present in a fluid is described in the article of Schultz et al. entitled "*A novel fluorescence-based array biosensor: Principle and application to DNA hydridization assays*", 2008, Biosens. Bioelectron. 23, 987-994.

This detector comprises a fluidic chamber in which a liquid circulates. The liquid is capable of containing different types of analytes of interest.

A surface of the fluidic chamber includes a plurality of two-dimensional detection areas onto which probe molecules are directly grafted. The probe molecules of each detection area are intended to react with a different type of analyte of interest. The surface receiving the detection areas is a surface of a transparent substrate.

The optical measurement device comprises a plurality of excitation light sources, each positioned orthogonally to the substrate and facing a different detection area, and a single optical collector positioned facing a side end of the substrate.

Thus, when the liquid flows into the fluidic chamber, it comes into contact with two-dimensional detection areas. The probe molecules of the detection areas react with the analytes of interest, according to the type of analyte.

The excitation light sources successively illuminate the detection areas. The probe molecules having reacted with an analyte respond to the corresponding light excitation by emitting a fluorescence light signal. This signal is refracted in the transparent substrate and then transmitted inside the latter, by internal total reflection, as far as the optical collector. By successive excitation of the detection areas, it is possible to avoid any interference of the light signals emitted by the different detection areas.

However, this detection system has a particularly limited operating time. On the one hand, the detection areas are two-dimensional areas, which strongly limits the amount of probe molecules per detection area. On the other hand, as each detection area is dedicated to a single category of analytes of interest, when the probe molecules of a same detection area have all reacted with the relevant analyte, the detection of this analyte is no longer possible.

DISCUSSION OF THE INVENTION

The object of the invention is to present a system for detecting analytes of interest present in a gas sample, at least partly finding a remedy to the drawbacks mentioned above relating to the designs of the prior art.

To do this, the object of the invention is a system for detecting analytes of interest present in a gas sample.

According to the invention, the detection system comprises:
- a layer of porous material, positioned at the surface of a substrate so as to extend longitudinally along a fluidic flow path of the gas sample, said porous material containing a plurality of probe molecules, each probe molecule being able to react with the analyte of interest by causing a change in the spectral properties of said probe molecule;
- means for generating a flow of the gas sample along said fluidic path, so that the gas sample comes into contact with said porous material layer; and
- at least one optical detection device capable of successively detecting at distinct detection areas of said porous material layer distributed along said fluidic path, a change in the spectral properties of at least one of said probe molecules.

By probe molecule, is meant a molecule specific to an analyte of interest which may react with the latter. The reaction between the probe molecule and said analyte causes a change in the spectral properties of the probe molecule.

The probe molecule applied within the scope of the present invention has fluorogenic or chromogenic properties when it interacts with a specific analyte.

Within the scope of the invention, the change in the spectral properties of the probe molecule is optically detectable when the probe molecule is subject to a light excitation signal with a given wavelength or over a given spectrum of wavelengths.

By optically detectable, is meant that the probe molecule subject to a light excitation signal emits as a response a light signal, because of its fluorogenic or chromogenic properties.

By change in the spectral properties, is meant a change in the wavelength of the absorption and/or fluorescence maxima, or even a reduction or an increase in the absorption and/or fluorescence intensity at a given wavelength.

The change in the spectral properties is inferred by comparing the spectral characteristics of the response signal of the probe molecule having reacted with a specific analyte to an excitation signal, with so-called reference spectral characteristics of the response signal of the probe molecule having not reacted with said analyte of interest to a same excitation signal.

The probe molecules may be directly or indirectly characterized by spectral absorption and/or fluorescence properties. A probe molecule may thus be directly characterized by spectral properties, when the signal of response to the excitation signal is emitted by the actual probe molecule. Moreover, a probe molecule may be indirectly characterized by spectral properties, for example by means of the product of the reaction of the probe molecule with an analyte of interest. In this case, the spectral properties of the probe molecule before reacting with the specific analyte and the spectral properties of the product of the reaction between the probe molecule and said analyte may be compared in order to infer therefrom a change in the spectral properties of said probe molecule.

By fluidic flow path of the gas sample, is meant a three-dimensional area which extends along a given direction, in which the gas sample is intended to flow.

By distinct detection areas, are meant spatial areas of the porous material layer, different from each other. They may nevertheless overlap partially.

Thus, the detector according to the invention comprises a porous material layer. The layer is three-dimensional on the one hand and has a plurality of pores into which the gas sample may be introduced on the other hand.

The probe molecules are therefore positioned in the material, notably at the solid/gas interface of the material, and particularly at the pores. Thus, the analyte adsorbing and/or binding surface area with the probe molecules is particularly high.

Further, the porous material layer extends longitudinally along the fluidic path. Therefore it does not have substantially any areas which are not or only very little covered by the flowing gas sample.

Unlike the first example of the prior art described earlier, the optical device of the detector according to the invention does not detect at the same time the changes in spectral properties at the whole of the porous material layer, but those successively detected at distinct detection areas of the porous material layer.

Moreover, insofar that the optical device successively detects the changes in spectral properties of probe molecules located in distinct areas distributed along the fluidic path, the emission rate of the response signal of the probe molecules having reacted is substantially constant at each of said detection areas. Also, the detector according to the invention has great resolution.

Further, insofar that the modifications of the spectral properties of the probe molecules of the different detection areas are not detected at the same time but successively according to the detection areas, the rate of emission of the response signal of the probe molecules having reacted is substantially constant over time. The detector therefore has a substantially constant sensitivity over time.

The porous material layer may extend along the fluidic path in a spatially continuous or discontinuous way. When it extends in a discontinuous way, it forms a succession of layer pads spatially distinct from each other.

Said material is preferably microporous or mesoporous. Microporous materials have an average pore size of substantially less than 20 Å, mesoporous materials have an average pore size comprised between 20 Å and 500 Å, macroporous materials having an average pore size of more than 500 Å, for example comprised between 50 nm and 100 μm. Preferably the material applied in the invention is microporous.

Said porous material may be a sol-gel. By <<a material of the sol-gel type>> or <<sol-gel material>>, both expressions being equivalent and interchangeable, is meant a material obtained by a sol-gel method consisting of using as precursors either identical or different metal alkoxides of formula $M(OR)_n(R')_m$ wherein M is a metal such as silicon, R and R' represent an alkyl group and m and n are integers with $m+n=4$, $2 \leq n \leq 4$ and $0 \leq m \leq 2$. The sol-gel materials are generally prepared in a solvent, which is preferably miscible with water and may be evaporated under mild conditions, in which the precursors are soluble. In the case of silicon alkoxides, mention may notably be made of alcohols, such as methanol, ethanol; ethers such as diethyl ether and tetrahydrofurane; chlorinated solvents, such as chloroform, $CH_2Cl_2$, $C_2H_5Cl_2$ or other aprotic solvents such as $CH_3CN$, acetone, methyl-ethylketone, or dioxane or protic solvents such as acetic acid, formamide. In the presence of water, hydrolysis of the alkoxide groups (—OR) occurs and the latter are transformed into silanol groups (Si—OH) which condense by forming siloxane groups (Si—O—Si). Small particles with a size generally of less than 1 nm are then formed. They aggregate and form lacunate clusters in suspension in the liquid: this is the sol. As polycondensation continues over time, the viscosity of the sol increases until it gels: the sol becomes a gel. A solid sol-gel material is obtained by drying the gel. During this step, the residual and interstitial solvents escape from the formed polymeric lattice and evaporate which causes contraction of the material. A final material is obtained, the volume of which is reduced as compared with the volume occupied by the sol. The sol therefore corresponds to a solution from which the material of interest to be deposited, in this case the sol-gel material, is obtained.

The sol-gel material applied within the scope of the present invention is essentially prepared from 1 to 4 alkoxysilane precursors and essentially obtained from hydrolysis of 1 to 4 alkoxysilane precursors. The sol-gel material applied within the scope of the present invention therefore essentially consists of units stemming from hydrolysis of a single alkoxysilane precursor or stemming from 2, 3 or 4 different alkoxysilane precursors.

As an alkoxysilane precursor which may be used within the scope of the present invention, mention may be made of tetramethoxysilane (TMOS), tetraethoxysilane (TEOS), tetrapropoxysilane (TPOS), tetrabutoxysilane (TBOS), methyl-trimethoxysilane (MTMOS), ethyl-trimethoxysilane (ET-MOS), propyltrimethoxysilane (PTMOS), methyltriethoxysilane (MTEOS), ethyltriethoxy-silane (ETEOS), propyltriethoxysilane (PTEOS), 3-aminopropyl-triethoxysilane (APTES), 3-aminopropyl-trimethoxysilane (APTMS), (3-(methyl-amino)propyl)-trimethoxysilane, 3-carboxypropyl-triethoxysilane, 3-carboxypropyltri-methoxysilane, 1,2-bis(triethoxy-silyl)ethane, 1,2-bis(trimethoxy-silyl)ethane, (3,3,3-trichloropropyl)triethoxysilane, 3,3,3-trifluoro-propyl-trimethoxysilane and mixtures thereof.

Advantageously, the alkoxysilane precursor applied within the scope of the present invention is TMOS.

The sol-gel material may further contain structuring compounds such as organic polymers like ionomers and notably fluorinated organic polymers derived from ethylene with an acid function, such as NAFION®, and also generally neutral surfactants.

Regardless of the alternative, the final sol-gel material generally contains at most 95% by mass of derivatives of alkoxysilanes, notably at most 85% by mass of derivatives of alkoxysilanes and, in particular, from 60 to 80% by mass of derivatives of alkoxysilanes.

Advantageously, said material is a sol-gel nanoporous material based on metal oxides.

Said material may also be a polymeric porous material. By <<polymeric material>>, is meant, within the scope of the present invention, a natural or synthetic, soluble or insoluble and notably organic (co)polymer. The polymeric material used in the present invention may be a hydrogel.

Thus, the polymeric material which may be used within the scope of the present invention is selected from agarose; gelatine; cellulose; carboxy-methylcellulose; an alginate; a polyolefin; a styrene polymer such as an advantageously porous polystyrene resin, a halogenated hydrocarbon polymer such as polytetrafluoroethylene or poly(chlorotrifluoroethylene); a vinyl polymer such as poly(vinyl decanoate) or polyvinyl alcohol; a (meth)acrylic polymer such as poly(n-butyl acetate) or a poly(benzyl methacrylate); polyethylene glycol; poly(propylene fumarate); poly(ethylene fumarate); poly(alpha-hydroxyester); poly(orthoester); a polyanhydride; a poly(phosphazene); a poly(ester amide); a polylactic acid; a polyglycolic acid; polycaprolactone (PCL); polydioxanone (PDO); polyurethane; a gel of cholesteryl anthraquinone-2-carboxylate and polymethylsiloxane; a gel of 1,3:2,4-dibenzylidene-sorbitol and of octamethylcyclotetrasiloxane; a gel of an aromatic diamide with a perfluorinated chain and of perfluorotributylamine notably described in the article of Loiseau et al., "*A fluoroponytails containing organogelator: gelation of perfluorotributylamine and isopropopanol*", 2002, Tetrahedron, Vol. 58, pages 4049-4052.

The substrate present in the detector according to present invention is a substantially planar solid substrate. Said substrate may be transparent or translucent, i.e. letting through light.

As an example of a substrate, mention may be made of a biochip support or a microscope slide such as those conventionally used in silicon, in glass, in metal, in polymer or in plastic. It may be of various sizes and shapes.

The substrate may, prior to receiving the porous material layer, have undergone a preparatory treatment so as to modify and/or to improve, the hydrophilic or hydrophobic properties of its surface. This treatment may consist in a chemical modification of the surface of the support by treatments such as oxidizing treatments or by depositing a coating on the surface with the customary deposition techniques known to one skilled in the art. This coating may for example be silicon; glass; silicon dioxide or a (per)fluorinated polymer.

One skilled in the art is aware of different probe molecules which may used within the scope of the present invention and known for detecting specific volatile analytes such as an aldehyde, formaldehyde, acetaldehyde, naphthalene, a primary notably aromatic amine, indole, scatole, tryptophan, urobilinogen, pyrrole, benzene, toluene, xylene, styrene, naphthalene and volatile biomarkers such as 1-methyl naphthalene, p-methyl anisate, methyl nicotinate and o-phenyl anisole. Such probe molecules are notably selected from enaminomers and from corresponding β-diketone/amine pairs, imines and hydrazines, 4-aminopent-3-en-2-one (Fluoral-P), croconic acid and probe molecules with an aldehyde function which are p-dimethylaminobenzaldehyde (DMABA or DAB), p-dimethylaminocinnamaldehyde (DMACA), p-methoxybenzaldehyde (MOB) and 4-methoxy-1-naphthaldehyde (MON), mixtures and salts derived from these compounds. Additional information on the probe molecules which may be used may be found in the international application WO 2007/031657 published on 22 Mar. 2007.

The probe molecules are notably found at the surface of the pores of the porous material. The probe molecules may be adsorbed at the surface of the pores of this material and/or bound to this surface through non-covalent bonds (hydrogen bonds or ionic bonds) and/or through covalent bonds.

The weight percentage of probe molecules is advantageously from 0.01 to 30%, in particular from 0.1 to 20% and most particularly from 1 to 10% based on the total weight of the polymeric porous material or of the sol-gel type.

Advantageously, said optical detection device comprises:
at least one excitation light source for successively illuminating said detection areas,
at least one optical collector for receiving at least one light signal from at least one of said probe molecules contained in the successively illuminated detection areas, in response to said corresponding light excitation signal, and calculation means for calculating a change in the spectral properties of at least one of said probe molecules, from said response light signal received beforehand.

Said calculation means advantageously calculate the value of at least one spectral quantity of the response signal received beforehand, and compare the thereby calculated value to a reference value of the same spectral quantity, thereby determining a change in the spectral properties of said probe molecule.

According to an embodiment of the invention, said at least one optical collector is capable of receiving the response light signal transmitted through the porous material layer or reflected by said porous material layer. The optical detection of the change in the spectral properties of at least one of said probe molecules is based on absorption spectroscopy techniques.

According to another embodiment of the invention, said at least one optical collector is capable of receiving the response light signal emitted by fluorescence by at least one probe molecule of the porous material layer having reacted with an analyte of interest. The optical detection of the change in the spectral properties of at least one of said probe molecules is based on fluorescence emission spectroscopy techniques.

Said at least one excitation light source and said at least one optical collector may be positioned facing each other with respect to the porous material layer, said substrate being transparent or translucent.

Alternatively, the optical measurement device may comprise a plurality of excitation light sources each positioned facing a distinct detection area of said porous material layer substantially orthogonally to the latter, and a single optical collector positioned facing a side end of said substrate, said substrate being transparent or translucent.

Moreover, the detection system according to the invention may comprise a plurality of porous material layers, each layer being dedicated to the detection of a different category of analyte of interest. Each of said layers is spatially distributed over said substrate according to a given pattern. More specifically, each of said layers is positioned at the surface of said substrate so as to longitudinally extend along a fluidic flow path of the gas sample. Each porous material contains a plurality of probe molecules, each probe molecule being able to react with an analyte of interest of a determined category, optionally distinct from that of the neighboring porous material layers, while causing a change in the spectral properties of said probe molecule.

The invention also relates to a method for making a system for detecting analytes of interest present in a gas sample according to any of the previous characteristics, comprising a step for forming said porous material layer at the surface of said substrate characterized in that it comprises the steps consisting of:

delimiting by photolithography, at the surface of said substrate, at least one localized site and with a defined shape extending longitudinally along said fluidic path, wettable by a solution containing said material or from which said material is obtained, the areas surrounding said site being non-wettable by said solution;

depositing on said site and said areas, said solution; by means of which said material is obtained at said site.

Wettability is defined by the contact angle or connection angle, formed by a drop of the solution with the substrate at the deposition site of this drop.

Thus, when it is specified that a site of the surface of the substrate is wettable with respect to the solution, this generally means that a deposited drop of the solution will form relatively to the deposition site a contact angle generally having a value of less than 90° while, for the non-wettable areas surrounding said site, this means that the contact angle formed between a drop of the solution and these areas generally has a value of more than 90°. From a practical point of view, this means that the solution, when it is deposited on the whole of the surface of the substrate, is concentrated at the wettable sites by this solution and does not remain or only very little at the non-wettable areas.

Further, the invention relates to a method for detecting analytes of interest present in a gas sample, characterized in that:

a flow of the gas sample is generated along a fluidic flow path, so that the gas sample comes into contact with a layer of a porous material, said layer being positioned on a surface of a substrate so as to extend longitudinally along said fluidic path, said porous material containing a plurality of probe molecules, each probe molecule being able to react with the analyte of interest by causing a change in the spectral properties of said probe molecule; and a change in the spectral properties of at least one of said probe molecules is successively detected by an optical detection device, at distinct detection areas of said porous material layer distributed along said fluidic path.

The optical detection step may consist of:

successively illuminating said detection areas along said fluidic path, by means of at least one light excitation source; and receiving at least one light signal from at least one of said probe molecules contained in the successively illuminated detection areas, by means of at least one optical collector, in response to said corresponding excitation light signal; and calculating a change in the spectral properties of at least one of said probe molecules, from said response light signal received beforehand.

Said calculation step may comprise the calculation of the value of at least one spectral quantity of the response signal received beforehand, and comparing the thereby calculated value with a reference value of the same spectral quantity, thereby determining a change in the spectral properties of said probe molecule.

Other advantages and characteristics of the invention will become apparent in the non-limiting detailed description below.

SHORT DESCRIPTION OF THE DRAWINGS

Embodiments of the invention will now be described as non-limiting examples, with reference to the appended drawings, wherein.

DETAILED DISCUSSION OF A PREFERRED EMBODIMENT

Figure 1:
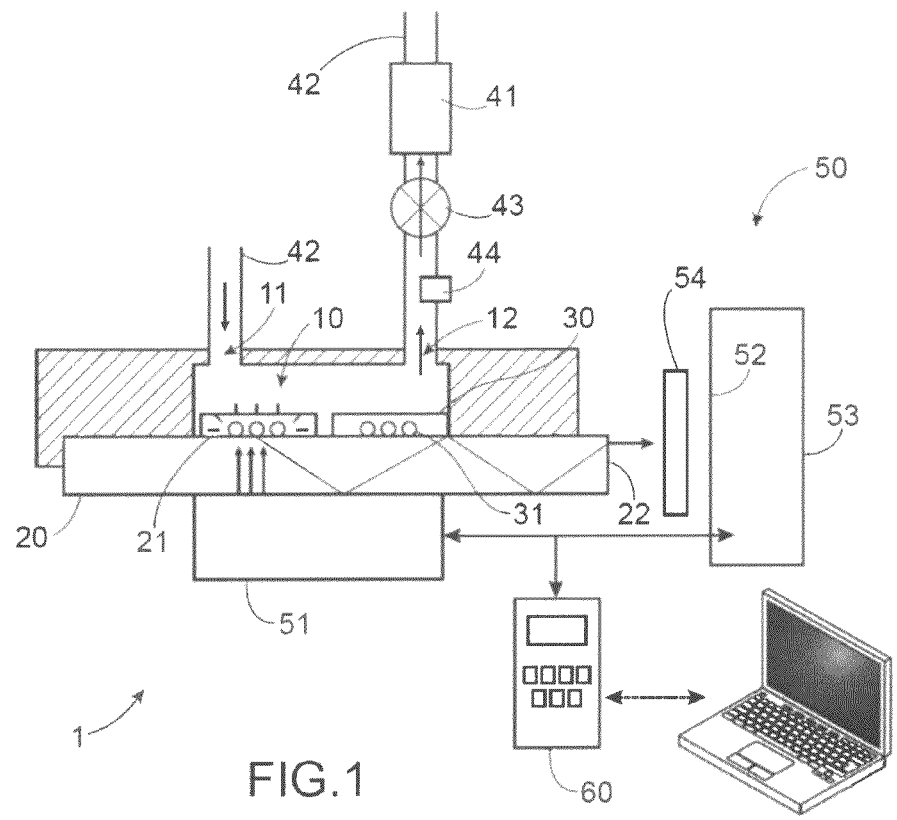
FIG. 1 is a schematic sectional view of a detection system according to the preferred embodiment of the invention.

In FIG. 1 a system 1 is illustrated for detecting analytes of interest present in a gas sample according to a preferred embodiment of the invention.

The detector 1 comprises a fluidic chamber 10 provided with a gas inlet orifice 11 and a gas outlet orifice 12. Both of these orifices 11, 12 are positioned so as to define inside the fluidic chamber and cooperating with the interior walls of the latter, a fluidic flow path for the gas sample.

Figure 2:
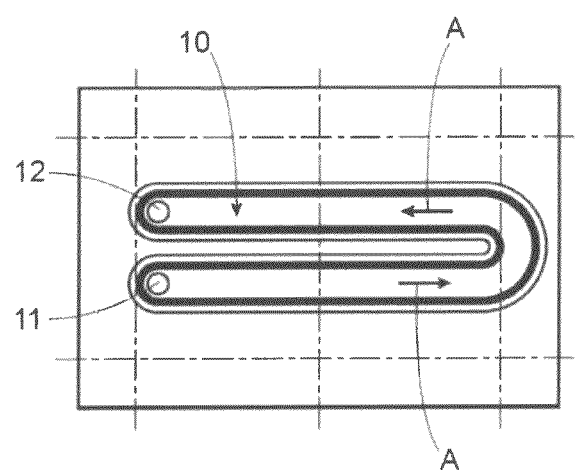
FIG. 2 is a schematic top longitudinal sectional view of the fluidic chamber including a gas inlet orifice and a gas outlet orifice.

As shown in FIG. 2, the fluidic chamber 10 may extend in a rectilinear way and include a curved portion. The direction of the fluidic path is given by the arrow A.

The fluidic chamber 10 comprises a planar solid substrate 20, a surface 21 of which forms at least partly one of the interior walls of the fluidic chamber 10 (FIG. 1). The substrate 20 may be a microscope glass slide.

The substrate 20 is here transparent or translucent, and thus lets through light.

On said surface 21 of the substrate 20 is positioned a layer 30 of porous material, so that the porous material layer 30 extends longitudinally along said fluidic path.

The porous material layer 30 thereby forms a localized deposit on the surface 21 of the substrate 20 and has a defined shape.

The porous material contains a plurality of probe molecules 31, each probe molecule 31 being able to react with the analyte of interest. Said reaction causes change in the spectral properties of the relevant probe molecule 31.

The probe molecules 31 are thus present at the surface of the porous material, in particular at the pores of the material. The detector according to the invention therefore has a surface for adsorbing and/or binding specific analytes with the probe molecules, which is particularly large. This surface area is typically comprised between 200 and 800 $m^2 \cdot g^{-1}$, notably between 300 and 700 $m^2 \cdot g^{-1}$ and, in particular between 400 and 600 $m^2 \cdot g^{-1}$ The detector according to the invention comprises means for generating a flow of the gas sample along said fluidic path.

A pump 41 is thus positioned upstream or downstream from the fluidic chamber 10, at tubes 42 for distributing the gas sample, connected to the inlet 11 and outlet 12 orifices of the fluidic chamber 10. The pump 41 allows a flow of the gas sample to be generated in the distribution tubes 42 and thus in the fluidic chamber 10.

A solenoid valve 43 and a flowmeter 44 may be positioned in series with the pump 41 at the distribution tubes 42, in order to check and control the gas flow in the tubes 42.

The detection system 1 according to the invention also comprises an optical detection device 50 capable of successively detecting, at distinct detection areas of said porous material layer 30 distributed along said fluidic path, a change in the spectral properties of at least one of said probe molecules.

More specifically, the optical device 50 comprises at least one excitation light source 51 for successively illuminating said detection areas, at least one optical collector 52 for receiving at least one light signal from at least one of said probe molecules 31 contained in the successively illuminated detection areas in response to the corresponding excitation light signal, and calculation means 53 for calculating any change in the spectral properties of at least one of said probe molecules 31, from said response light signal received beforehand.

Figure 3:
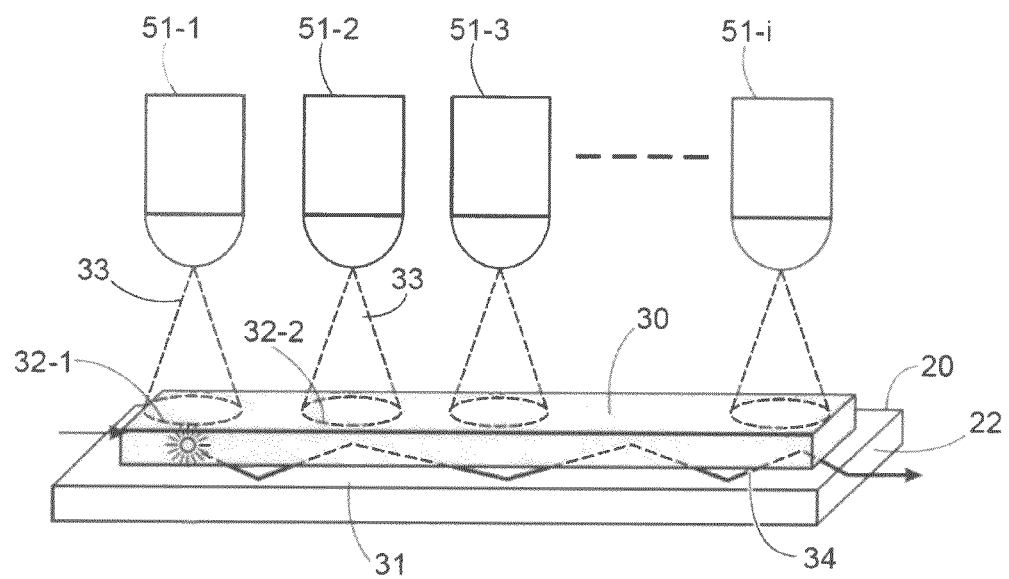
FIG. 3 is a schematic partial perspective view of the porous material layer facing which a plurality of excitation light sources is positioned, the layer being spatially continuous.

As illustrated in FIG. 3, a plurality of excitation light sources 51 is positioned along the porous material layer 30, along the longitudinal axis of the latter.

The excitation sources 51 may be light-emitting diodes (LEDs), each positioned substantially orthogonally to the substrate 20, so as to be each able to illuminate a portion of the porous material layer 30 by emitting an excitation light signal 33. Each of these portions then forms a detection area 32. The detection areas 32 are thus distributed along the longitudinal axis of the porous material layer 30.

In the case of a transparent or translucent substrate 20, the diodes 51 are advantageously positioned opposite to the porous material layer 30 relatively to the substrate 20.

The optical collector 52, for example a photomultiplier, a photodiode, a CCD sensor or even a CMOS sensor, is positioned so that its optical axis for receiving light signals is substantially comprised in the median plane of the substrate 20. By median plane of the substrate, is meant the plane substantially orthogonal to the thickness dimension of the substrate 20 and extending inside the substrate 20.

Thus, the optical collector 52 is positioned facing a side face 22 of the substrate 20 and in proximity to the latter.

An optical filter 54 may be placed between the side face 22 of the substrate 20 and the optical collector 52, allowing the light signals to be filtered according to their wavelength.

The optical device 50 further comprises calculation means 53, connected to the optical collector 52, allowing calculation of the value of at least one spectral quantity of the received light signal 34, and comparison of the thereby calculated value with a reference value of the same spectral quantity.

Thus, the reference value of the spectral quantity characterizes the spectral properties of absorption and/or fluorescence of the probe molecules before reaction with the analyte of interest.

The reference spectral quantity may be the wavelength of the absorption and/or fluorescence maxima, or even a decrease or an increase in the absorption and/or fluorescence intensity at a given wavelength.

A difference between the calculated value and the reference value of the spectral quantity gives the possibility of inferring a change in the spectral properties of at least one of said probe molecules and thus the presence of an analyte of interest in the gas sample.

The calculation means 53 conventionally include a microprocessor, a random access memory and/or a random access memory or a memory card. Thus, the received light signals 34 by the collector 52 are analyzed so as to extract therefrom a value of a spectral quantity characteristic of the spectral properties of the probe molecule, which is then compared with a reference value.

The detector 1 according to the invention also comprises control means 60, connected to the pump 41 and to the solenoid valve 43 on the one hand and to the optical detection device 50 on the other hand, allowing synchronous control of the sequence of generation of flow of the gas sample and of the sequence for emitting an excitation light signal 33 at the detection areas 32 and receiving a response signal 34. The control means 60 may thus comprise a micro-controller card.

Moreover, a visual or audio alarm (not shown) may be present in order to inform a user when for example the rate of detected analytes of interest exceeds a predetermined threshold value.

The fluidic chamber 10 may have a width from a few tenths of millimeters to a few tens of millimeters, for example from 0.5 mm to 100 mm, and a length of a 100 mm. The length is defined according to the direction A of the fluidic path and the width along an axis orthogonal to the direction A of the fluidic path.

It may be machined in a neutral and black material, for example stainless steel 2017A coated with a layer of black Teflon of reference ISANA P2.

As described earlier, the substrate 20 may be a microscope glass slide.

The porous material layer 30 may have a width comprised between a few microns and a few tens of millimeters, for example between 10 µm and 50 mm. Its thickness may be comprised between 30 nm and a few hundred microns, for example 500 µm, and preferably be comprised between 100 nm and 5 µm.

The porous material may be a sol-gel porous material obtained from tetramethoxysilane (TMOS or tetramethylorthosilicate) and comprising Fluoral-P as probe molecule. Such a material is described in international application WO 2007/031657 published on 22 Mar. 2007.

The detected analyte may then be an aldehyde, i.e. an organic molecule with a terminal carbonyl function, such as for example, formaldehyde, acetaldehyde, propionaldehyde, butyraldehyde, acrolein, pentanal, hexanal and benzaldehyde.

The operation of the detection system according to the invention is the following, with reference to FIG. 3.

A gas sample flow is generated in the fluidic chamber 10. The gas sample enters the fluidic chamber through the inlet orifice 11, flows along the fluidic path in the direction A, and flows out of the fluidic chamber 10 through the outlet orifice 12.

The admission of the gas sample into the fluidic chamber 10 is accomplished preferably sequentially. Thus, the flow may be generated for a few minutes, for example 3 min, and then stopped for a few minutes, for example 5 min to 10 min. The flow generation/flow absence sequence is repeated several times. The flow rate of the pump 41 may be comprised between 10 ml/min to a few hundred milliliters per minute.

The gas sample will then naturally come into contact with the porous material layer 30 and is introduced inside the latter, because of the porosity of the material.

The analytes of interest are adsorbed and/or bound with the probe molecules 31 contained in the porous material layer 30, particularly those located at the surface of the pores of the material.

The diodes 51 successively illuminate the detection areas 32 of the porous material layer 30, along the fluidic path, along the direction A of flow of the gas sample.

Thus, a first diode 51-1 illuminates a first detection area 32-1 located as far upstream as possible from the porous material layer 30.

The probe molecules 31 having reacted with a specific analyte are then excited by the excitation light signal 33 emitted by the first diode 51-1. By excitation of a probe molecule having reacted, is equally meant the excitation directly from the probe molecule having reacted, or the excitation indirectly from the probe molecule having reacted, more specifically from the product of the reaction between the probe molecule and the specific analyte.

In the case of detection by fluorescence, the probe molecule 31 having reacted has itself or the product of the reaction, fluorogenic properties.

The probe molecule 31 having reacted is then excited by an excitation signal 33 emitted by the diode 51-1 according to a suitable wavelength.

Thus, DDL (3,5-diacetyl-1,4-dihydrolutidin), a product of the reaction between Fluoral-P (4-amino-3-penten-2-one) and formaldehyde, may be excited by a light signal 33 of wavelength 415 nm. It emits as a response, a maximum intensity light signal 34 at 502 nm.

The response light signal 34 emitted by the DDL is refracted in the transparent substrate 20 and then transmitted by internal total reflection as far as the optical collector 52.

The filter 54 placed between the substrate 20 and the collector 52 allows selection of the response light signals 34 having the fluorescence wavelength of the DDL, here 502 nm.

The fluorescence spectra of the probe molecule having reacted are compared with the fluorescence spectrum of the probe molecule before reaction. A difference between both spectra, for example a change in the wavelength of the maximum fluorescence intensity, or even a decrease or an increase in the fluorescence intensity at a given wavelength allows inference of the presence of an analyte of interest in the gas sample.

It is also possible to achieve detection by absorbance spectroscopy.

Thus, the probe molecule, here Fluoral-P, has an absorption spectrum, the maximum intensity of the signal of which corresponds to 302 nm, while the DDL has two intensity peaks, one at 206 nm and the other at 415 nm. The detection may then be achieved by measuring the absorbance change at 415 nm, where only DDL is absorbent.

Thus, the first diode 51-1 illuminates the first detection area 32-1 for a predetermined time $T_1$, until for example substantially all the probe molecules 31 capable of reacting with analytes have reacted. The first diode 51-1 then stops the illumination of the first detection area 32-1.

Next, optionally after a pause period, the second diode 51-2 illuminates the second detection area 32-2, neighboring the first area 32-1 and positioned downstream from the latter along the direction A of flow of the gas sample, during a predetermined illumination period $T_2$.

The optical detection step, by fluorescence and/or by absorbance, is renewed. The second diode 51-2 thus emits an excitation light signal 33 for exciting the probe molecules having reacted and located in the second detection area 32-2. The latter then emit a response light signal 34 which is received by the optical collector 52. The change in the spectral properties of the probe molecules is measured, as described earlier, which allows inference of the presence of analytes of interest at the second detection area 32-2.

The detection method is then continued, as earlier, depending on the number of diodes 51 positioned along the porous material layer 30.

The illumination period $T_1, T_2 \ldots$ of the detection areas 32-1, 32-2 ... may be determined beforehand by calibration.

As mentioned earlier, each illumination period may correspond to the required time for substantially all of the probe molecules 31 present in each detection area 32-1, 32-2 ... and capable of reacting with the analytes to have reacted.

Alternatively, each illumination period may be determined so as to optimize the sensitivity of the detector at each of said detection areas 32-1, 32-2 ....

Figure 8:
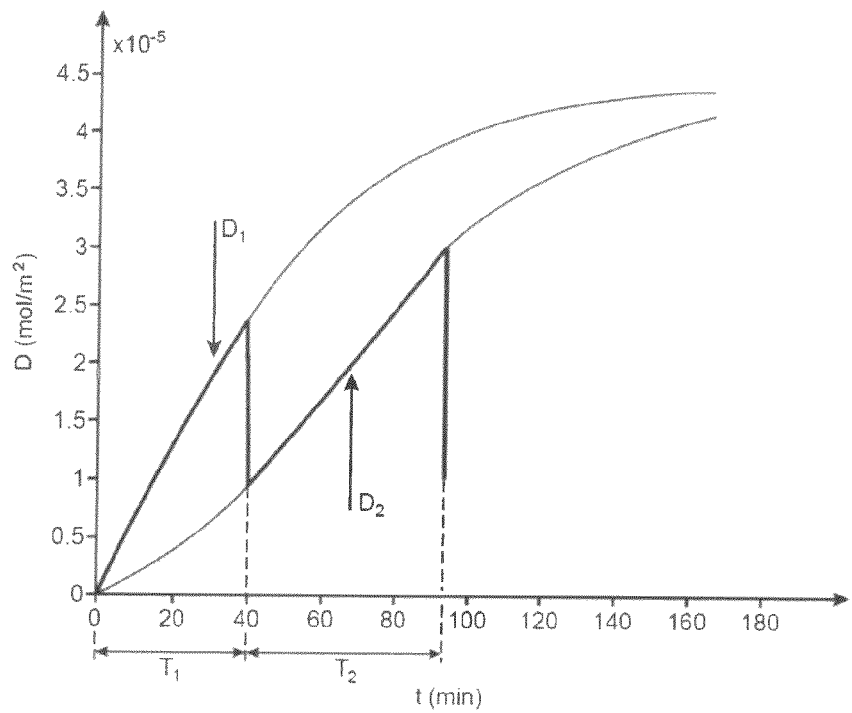
FIG. 8 illustrates an example of the time-dependent change in the concentration of DDL (3,5-diacetyl-1,4-dihydrolutidine) at two detection areas of the porous material layer, within the scope of a method for calibrating the detection system.

In this respect and as an illustration, FIG. 8 illustrates the time-dependent change in the DDL concentration at two detection areas of the porous material layer. Both of these detection areas include a same concentration of probe molecules, here Fluoral-P.

A gas flow including a constant formaldehyde level is generated. Formaldehyde then reacts with the Fluoral-P present in both detection areas in order to produce DDL.

The DDL produced in the detection areas is then excited by an excitation light signal emitted by a diode. It should be noted that the light signal simultaneously illuminates both detection areas, so as to be able to detect the time-dependent change of the concentrations D1, D2 of DDL present in both of the detection areas (FIG. 8).

By analyzing this time-dependent change, it is possible to determine a period $T_i$ for each detection area i during which the time-dependent change in the DDL concentration has a high slope.

It is thus possible to define this period $T_i$ as being the optimum illumination period for which, at each detection area i, the sensitivity of the detector is maximum.

This period $T_i$ may be obtained by the following condition:

$$T_i / \forall t, \partial_t D_i \leq p_i$$

wherein $p_i$ is a slope criterion relating to each detection area i. It may assume a value which is identical or different for each area i and therefore each curve $D_i(t)$. The slope $p_i$ may be the largest slope value for a given period.

Thus, the period $T_i$ for illumination of each detection area 32-i carried out by each diode 51 is determined beforehand by this calibration method and thereby allows the detector to have high sensitivity.

By illuminating each detection area i during each illumination period $T_i$, substantially corresponding to a predetermined slope of the curve $D_i$, a stable detection sensitivity is obtained over time. In the example of FIG. 8, the area 1 may thus be illuminated between $t_0$ and $t_0+40$ minutes, and the area 2 between $t_0+40$ minutes and $t_0+90$ minutes. The instant $t_0$ then corresponds to the 0 abscissa of the graph of curve 8: this is the instant when a gas to be analyzed is injected into the detection system, the detection areas not having been exposed beforehand or negligibly to the analyte of interest to be detected.

On the other hand, the curves $D_i(t)$ of FIG. 8 show that the sensitivity of each detection area changes over time. Thus, the sensitivity of the pad i, at instant t may be quantified by the slope of each curve $D_i(t)$, for example the largest slope value for a given period. Let us specify that each curve may be determined experimentally by using a detection system dedicated to calibration, or by simulation. By having detection areas for which sensitivity varies in a known way, depending on time, it is possible to increase the measurement dynamic range, by activating a not very sensitive detection area when the concentration of the analyte is high, and so that the most sensitive detection areas produce a saturated light signal. Conversely, when the concentration of the analyte of interest is low, the most sensitive detection area is enabled.

With the detection system according to the embodiment which has just been described it is not only possible to detect the presence of analytes of interest in the gas sample but also to quantify the latter, or even trap them.

Thus, the calculation means 53 of the optical device 50 may determine the amount of probe molecules 31 which have reacted with an analyte of interest by correlation with the intensity of the response light signal 34 received by the collector 52.

Further, the analytes of interest adsorbed and/or bound to the surface of the porous material layer 30 are captured by the latter. The porous material layer 30 then acts as a filter for analytes, the latter may be harmful and present in a contaminated environment.

Figure 4:
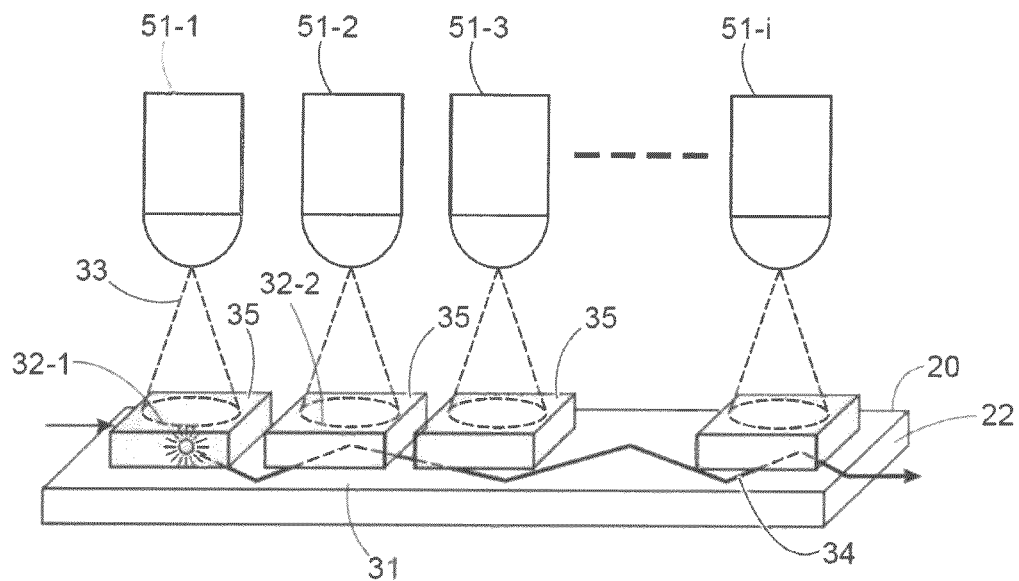
FIG. 4 is a schematic partial perspective view of the porous material layer facing which a plurality of excitation light sources is positioned, the layer being spatially discontinuous.

As illustrated by FIG. 4, the porous material layer 30 may extend in a spatially discontinuous way at the surface 21 of the substrate 20. The porous material layer 30 thus comprises a plurality of pads 35 of porous material, spatially distinct and distributed along the fluidic path.

The surface of each pad 35 substantially coincides with the surface of each detection area 32 delimited by the respective illumination area of the excitation light source(s) 51. The volume of each pad may be comprised between 50 $\mu m^3$ and 200 $mm^3$ and, preferably between 100 $\mu m^3$ and 5 $mm^3$.

Moreover, as an alternative to a plurality of excitation light sources, a single excitation source 51 may be used, for example a single diode 51, capable of successively illuminating said detection areas 32.

The single diode 51 may be translationally mobile along a direction parallel to that of the fluidic path. The single diode 51 may also be fixed, a set of lenses and mirrors being positioned between the diode 51 and each detection area 32, in order to ensure successive illumination of the different detection areas 32.

Further, a plurality of collectors 52 may be used, for example in an amount of one collector 52 per excitation light source 51. Each collector 52 may be positioned facing the corresponding excitation light source 51, oppositely to the latter relatively to the porous material layer 30 and to the substrate 20.

Finally, the detector according to the invention may comprise a plurality of porous material layers 30 positioned on the surface 21 of the substrate 20, each layer 30 being intended to detect a different category of analyte.

Thus, said porous material layers 30 may extend along the fluidic flow path of the gas sample, in a parallel way with respect to each other.

Each porous material thus comprises a different category of probe molecule, each probe molecule category being capable of reacting with a specific analyte category.

The detector may then comprise a plurality of optical devices 50, identical with or similar to the one described earlier, each being intended to successively detect, at the detection areas 32 of the corresponding porous material layer 30, a change in the spectral properties of at least one of said probe molecules.

The porous material layer 30 of the detector according to the invention may be made in the following way, with reference to FIGS. 5 to 7.

In this example, the substrate is a glass slide. The resin used is TELR-P0003PV (propylene glycol monomethyl ether acetate, Tokyo Ohka Kogyo Co. Ltd), the viscosity of which is equal to 5 mPa·s (FIG. 5, step (a)). After depositing the resin by means of a spin coater, a baking step is required in order to rapidly remove part of the solvents and to ensure polymerization of the matrix. This annealing is carried out for 1 min, at the temperature of 110° C.

Figure 5:
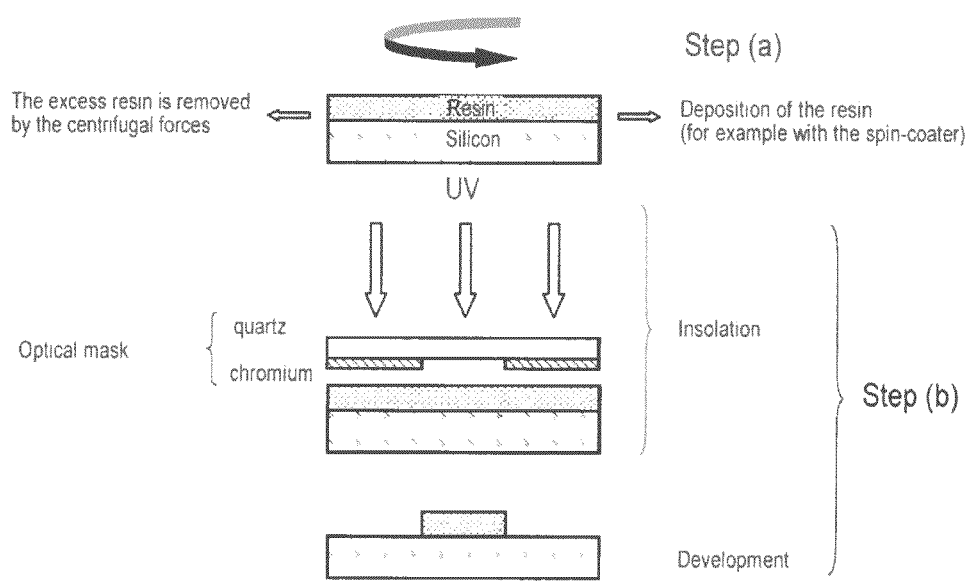
FIG. 5 shows a schematization of steps (a) and (b) of the method for forming the porous material layer according to an embodiment applying a glass substrate, a hydrophilic material to be deposited of the sol-gel type containing a probe molecule and a positive photoresist.

Insolation consists in the exposure of certain areas of the resin, via a masking system, to ultraviolet radiation (FIG. 5, step (b)).

With the mask it is possible to define the portion of the surface of the substrate on which will extend the porous material layer. This surface portion extends longitudinally along the fluidic path for the flow of the gas sample.

The mask applied is a photolithographic mask made in quartz and in chromium. Insolation is carried out with a high pressure apparatus of the MA8 type, the insolation time is 20 s at a power of 390 W.

The resin is then revealed by means of a developer TMA 238 provided by JSR. This developer is a basic aqueous solution (normality 0.28 N) conventionally containing tetramethylammonium hydroxide, KOH and NaOH. It allows removal of the insolated resin (FIG. 5, step (b)).

Next an annealing step is required in order to remove the residual solvents and to crosslink the resin. This annealing is carried out for 2 mins at 130° C.

The crosslinked remaining resin thus extends along the portion of the surface of the substrate intended for receiving the porous material layer.

After annealing, the substrate i.e. the glass slide, still has hydrophilic properties (contact angle (water)=35-40°). Thus, a silanization step (FIG. 6, step (c)) is contemplated in order to make the substrate hydrophobic. Before this silanization, the substrate is treated with oxygen plasma with a power of 600 W for 1 min so as to generate at its surface silanol groups.

The silanization is carried out by MVD (Molecular Vapor Deposition) with, like silane, (1H,1H,2H,2H)-perfluorodecyl-trichlorosilane (FDTS) of formula:

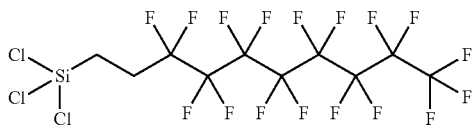 [SMILES: FC(F)(F)C(F)(F)C(F)(F)C(F)(F)C(F)(F)C(F)(F)C(F)(F)C(F)(F)CC[Si](Cl)(Cl)Cl]

In this step, deposition of a few nm of silane is achieved on the substrate. The drop angle is thus in the order of 108-110°.

Figure 6:
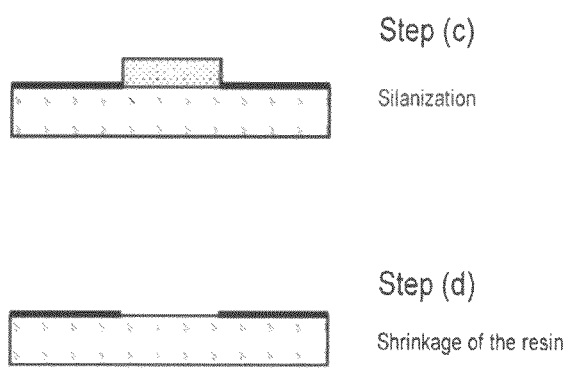
FIG. 6 shows a schematization of steps (c) and (d) of the method for making the porous material layer according to the embodiment of FIG. 5.
Figure 7:
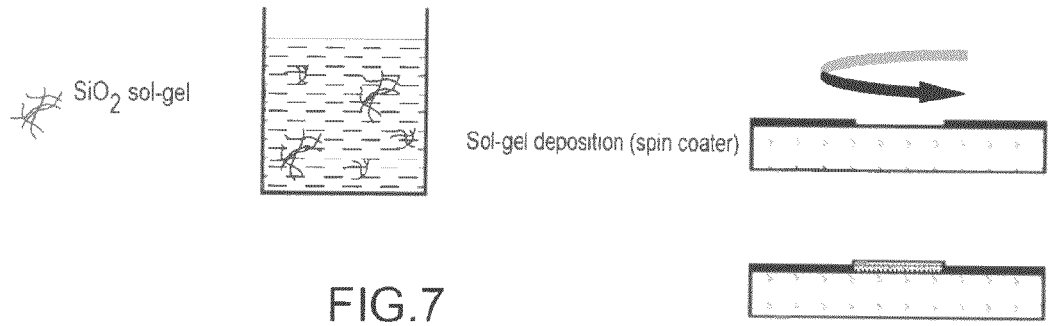
FIG. 7 shows a schematization of step (e) of the method according to the embodiment of FIG. 5, this step consisting in depositing the sol-gel material.

The resin is then removed (FIG. 6, step (d)), clearing the portion of the surface of the substrate intended to receive the porous material layer.

To do this, the substrate is rinsed for 10 min with acetone, with ultrasound, 10 mins with ethanol, with ultrasound and 10 mins with water with ultrasound and then dried by means of a centrifuge for 10 mins at 1,000 rpm. Subsequently to the rinsings, the deposited silane is not removed. The resin is thus removed and, at the location where the resin was localized, i.e. on the portion of the surface of the substrate intended to receive the porous material layer, the substrate is hydrophilic.

A sol-gel porous material comprising 4-amino-3-penten-2-one (Fluoral-P) is then deposited on the hydrophilic areas of the substrate.

This doped Fluoral-P material is obtained from a silica precursor, tetramethoxysilane (TMOS). Initially, 100 mg of Fluoral-P are dissolved by sonication in 1,030 µL of ethanol of spectroscopic quality. 651 µL of TMOS and 318 µL of millipore water (R=18 MΩ) are then added.

The thereby obtained 2 mL of sol are kept in a hermetically sealed pillbox (plug+Parafilm). The sol is again sonicated for 15 mins in order to avoid aggregation of the Fluoral-P molecules, and mechanically stirred until deposition.

The deposition of the sol is carried out by spin coating, with a deposition time of the order of 1 min and a rotary speed of the order of 2,000 revolutions per minute.

During the deposition of the sol over the whole surface of the substrate i.e. on the hydrophilic surface portion and the hydrophobic surface portion surrounding the hydrophilic portion (FIG. 7), the formed sol-gel is concentrated on the hydrophilic portion of the substrate, while occupying the whole possible space. Thus, on the hydrophobic portion, no trace of sol-gel is present.

Thus, a sol-gel porous material layer is obtained, the shape of which is well defined and the thickness is well controlled by the conventional spin coating deposition method. The porous material layer extends longitudinally along the fluidic path.

Of course, various modifications by one skilled in the art may be provided to the invention which has just being described, only as non-limiting examples.

The invention claimed is:

1. A detection system for detecting analytes of interest present in a gas sample, comprising:
   a layer of porous material, positioned at the surface of a substrate so as to extend longitudinally along a fluidic flow path of the gas sample, said porous material containing a plurality of probe molecules, each probe molecule being able to react with the analyte of interest by causing a change in the spectral properties of said probe molecule;
   a pump for generating a flow of the gas sample along the fluidic path so that the gas sample comes into contact with said layer of porous material; and
   at least one optical detection device capable of successively detecting, at distinct detection areas of said porous material layer distributed along said fluidic path, a change in the spectral properties of at least one of said probe molecules,
   wherein the optical detection device comprises
      a plurality of excitation light sources, wherein each excitation light source is positioned facing a different detection area, and
      at least one optical detector positioned for receiving at least one light signal from at least one of said probe molecules contained in the successively illuminated detection areas, in response to said corresponding excitation light signal, and wherein the excitation light sources successively illuminate the detection areas.

2. The detection system according to claim 1, wherein said material is microporous or nanoporous.

3. The detection system according to claim 1 or 2 wherein said material is a sol-gel or a polymer.

4. The detection system according to claim 1, wherein said material is a sol-gel nanoporous material based on metal oxides.

5. The detection system of claim 1, wherein said substrate is transparent or translucent.

6. The detection system according to claim 1, wherein said optical detection device further comprises:
   calculation means for calculating a change in the spectral properties of at least one of said probe molecules, from said response light signal received beforehand.

7. The detection system according to claim 6, wherein said calculation means calculate the value of at least one spectral quantity of the response light signal received beforehand, and compare the thereby calculated value with a reference value of the same spectral quantity, thereby determining a change in the spectral properties of said probe molecule.

8. The detection system according to claim 1, wherein said at least one optical detector is able to receive the response light signal transmitted through the layer of porous material or reflected by said layer of porous material.

9. The detection system according to claim 1, wherein said at least one optical detector is able to receive the response light signal emitted by fluorescence by at least one probe molecule of the layer of porous material having reacted with an analyte of interest.

10. The detection system according to claim 1, wherein in that said excitation light sources and said at least one optical detector are positioned facing each other relatively to the layer of porous material, said substrate being transparent or translucent.

11. The detection system according to claim 1, wherein it comprises a plurality of layers of porous material, each layer being dedicated to the detection of a different category of analyte of interest.

12. The detection system according to claim 1, wherein the optical detector is positioned substantially orthogonally to the substrate.

13. The detection system according to claim 1, wherein the optical detector is positioned facing a side end of the substrate.

14. A method for detecting analytes of interest present in a gas sample, wherein:
- a flow of the gas sample is generated along a fluidic flow path, so that the gas sample will come into contact with a layer of porous material, said layer being positioned on a surface of a substrate so as to extend longitudinally along said fluidic path, said porous material containing a plurality of probe molecules, each probe molecule being able to react with the analyte of interest by causing a change in the spectral properties of said probe molecule; and
- a change in the spectral properties of at least one of said probe molecules is successively detected by an optical detection device, at distinct detection areas of said layer of porous material, distributed along said fluidic path, wherein the optical detection device comprises
  - a plurality of excitation light sources, wherein each excitation light source is positioned facing a different detection area, and
  - at least one optical detector positioned for receiving at least one light signal from at least one of said probe molecules contained in the successively illuminated detection areas, in response to said corresponding excitation light signal, and
- wherein the excitation light sources successively illuminate the detection areas.

15. The detection method according to claim 14, wherein the optical detection step consists of:
- successively illuminating said detection areas along said fluidic path, with at least one excitation light source; and of
- receiving at least one light signal from at least one of said probe molecules contained in the successively illuminated detection areas, with at least one optical collector, in response to said corresponding excitation light signal; and of
- calculating a change in the spectral properties of at least one of said probe molecules, from said response light signal received beforehand.

16. The detection method according to claim 15, wherein the calculation step comprises the calculation of the value of at least one spectral quantity of the response signal received beforehand and the comparison of the thereby calculated value with a reference value of the same spectral quantity, thereby determining a change in the spectral properties of said probe molecule.

* * * * *